(12) United States Patent
Takenouchi

(10) Patent No.: US 12,390,087 B2
(45) Date of Patent: Aug. 19, 2025

(54) MEDICAL IMAGE PROCESSING DEVICE AND MEDICAL OBSERVATION SYSTEM

(71) Applicant: Sony Olympus Medical Solutions Inc., Tokyo (JP)

(72) Inventor: Yusuke Takenouchi, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 371 days.

(21) Appl. No.: 18/176,501

(22) Filed: Mar. 1, 2023

(65) Prior Publication Data

US 2023/0284872 A1 Sep. 14, 2023

(30) Foreign Application Priority Data

Mar. 8, 2022 (JP) ................................ 2022-035566

(51) Int. Cl.
*A61B 1/00* (2006.01)

(52) U.S. Cl.
CPC ...... *A61B 1/00009* (2013.01); *A61B 1/00006* (2013.01)

(58) Field of Classification Search
USPC ........................................................ 382/128
See application file for complete search history.

(56) References Cited

U.S. PATENT DOCUMENTS

| | | | |
|---|---|---|---|
| 11,942,213 B2 * | 3/2024 | Okada | A61B 1/00055 |
| 2011/0228167 A1 * | 9/2011 | Sasaki | G06T 5/70 |
| | | | 348/E5.077 |
| 2013/0278739 A1 * | 10/2013 | Tanaka | A61B 1/00057 |
| | | | 348/72 |
| 2015/0256804 A1 * | 9/2015 | Wen | H04N 9/646 |
| | | | 348/453 |
| 2020/0267347 A1 * | 8/2020 | Sudo | H04N 5/772 |

FOREIGN PATENT DOCUMENTS

JP 2007-312832 A 12/2007

* cited by examiner

*Primary Examiner* — Haris Sabah
(74) *Attorney, Agent, or Firm* — XSENSUS LLP

(57) ABSTRACT

A medical image processing device includes an image processing unit configured to perform image processing on a captured image obtained by capturing a subject image. The image processing unit includes: a memory configured to store the captured image; and a noise processing unit configured to enable execution of writing of the captured image into the memory and readout of the captured image from the memory individually, and execute noise reduction processing of reducing noise of the captured image of the current frame based on the input captured image of the current frame and the captured image of the past frame read out from the memory, the noise processing unit being configured to execute readout stop processing of stopping readout of the past frame from the memory at a predetermined timing and writing the captured image of the current frame into the memory without executing the noise reduction processing.

8 Claims, 7 Drawing Sheets

MEDICAL IMAGE PROCESSING DEVICE AND MEDICAL OBSERVATION SYSTEM

This application claims priority from Japanese Application No. 2022-035566, filed on Mar. 8, 2022, the contents of which are incorporated by reference herein in its entirety.

BACKGROUND

The present disclosure relates to a medical image processing device and a medical observation system.

In the medical field, there has been known a medical observation system that observes the inside of a subject (inside of a living body) (refer to JP 2007-312832 A, for example).

The medical observation system described in JP 2007-312832 A includes a noise processing unit that executes noise reduction processing, being processing of reducing noise of an input captured image of a current frame. Specifically, the noise processing unit executes noise reduction processing, being processing of reducing noise of the captured image of the current frame, based on the input captured image of the current frame and a captured image of the past frame read out from the memory.

SUMMARY

According to the technique described in JP 2007-312832 A, for example, in a case where the memory includes data of an indefinite value at the time of power startup or the like, the noise processing unit executes noise reduction processing across the input captured image of the current frame and the data of the indefinite value stored in the memory. In such a case, since appropriate data is not stored in the memory as the captured image of the past frame, the noise reduction processing, when being executed, would be inappropriate processing, leading to a failure in noise reduction and in the acquisition of an image suitable for observation.

DETAILED DESCRIPTION

Figure 1:
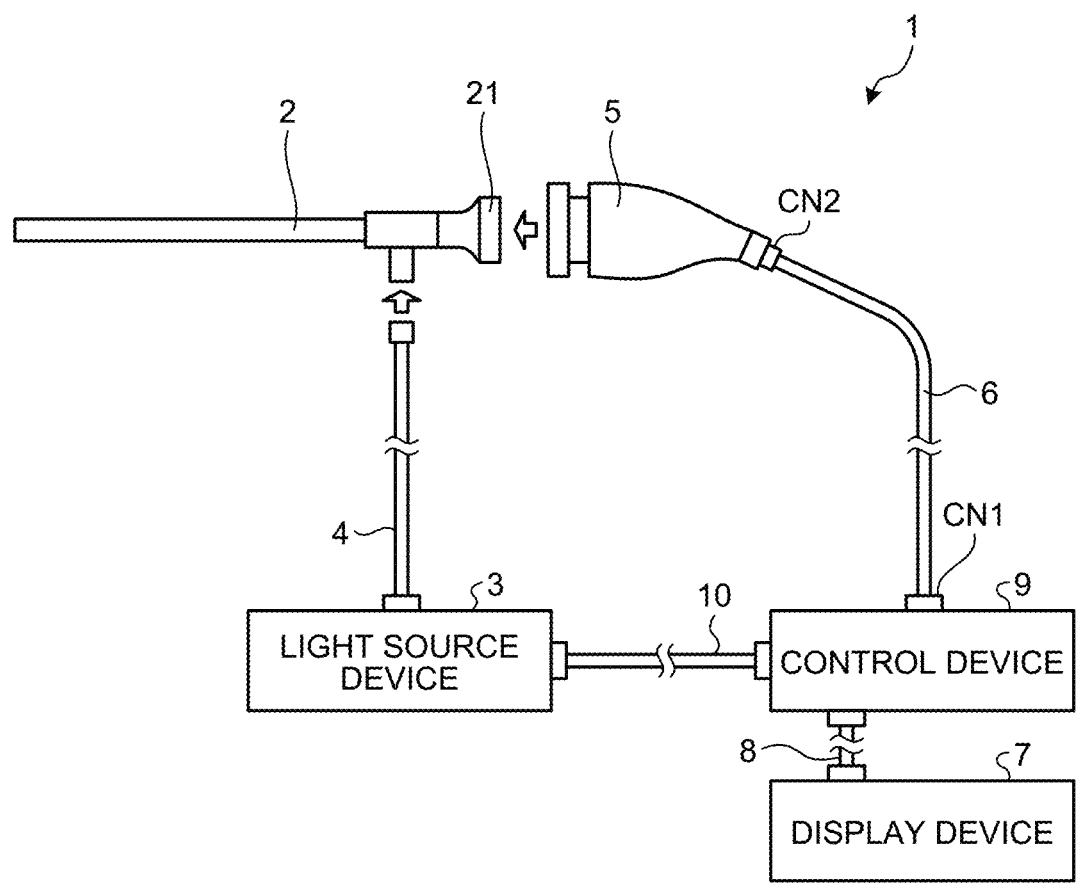
FIG. 1 is a diagram illustrating a medical observation system according to an embodiment.

Hereinafter, modes for carrying out the present disclosure (hereinafter referred to as embodiments) will be described with reference to the drawings. Note that the present disclosure is not limited to the embodiments described below. In the drawings, same reference signs are attached to the same components.

Schematic configuration of medical observation system

FIG. 1 is a diagram illustrating a configuration of a medical observation system 1 according to an embodiment.

The medical observation system 1 is a system that is used in the medical field and observes the inside of a subject (living body). As illustrated in FIG. 1, the medical observation system 1 includes an insertion unit 2, a light source device 3, a light guide 4, a camera head 5, a first transmission cable 6, a display device 7, a second transmission cable 8, a control device 9, and a third transmission cable 10.

In the present embodiment, the insertion unit 2 is implemented by a rigid endoscope. That is, the insertion unit 2 has an elongated shape that is entirely rigid, or partially rigid with a partially flexible portion, so as to be inserted into a living body. The insertion unit 2 includes an optical system (not illustrated) having one or more lenses and configured to collect light (subject image) from the living body.

The light source device 3 is connected to one end of the light guide 4, and supplies illumination light of a light amount designated by the control device 9 to the one end of the light guide 4 under the control of the control device 9. In the present embodiment, the light source device 3 is separated from the control device 9. However, the configuration is not limited to this, and it is allowable to employ a configuration in which the light source device 3 is provided inside the control device 9.

The light guide 4 has one end detachably connected to the light source device 3 and the other end detachably connected to the insertion unit 2. The light guide 4 transmits the light supplied from the light source device 3 from one end to the other end and supplies the light to the insertion unit 2. The light supplied to the insertion unit 2 is emitted from a distal end of the insertion unit 2 and directed into the living body. The light (subject image) applied to internal portions of the living body is condensed by the optical system in the insertion unit 2.

The camera head 5 corresponds to a medical observation device according to the present disclosure. The camera head 5 is detachably connected to an eyepiece 21 of the insertion unit 2. In addition, the camera head 5 captures a subject image condensed by the insertion unit 2 and generates an image signal (hereinafter, referred to as a captured image) under the control of the control device 9.

Note that a detailed configuration of the camera head will be described in "Configuration of camera head" described below.

The first transmission cable 6 has one end detachably connected to the control device 9 via a connector CN1 (FIG. 1), and has the other end detachably connected to the camera head 5 via a connector CN2 (FIG. 1). The first transmission cable 6 transmits the captured image or the like output from the camera head 5 to the control device 9, and transmits a control signal, a synchronization signal, a clock, power, or the like output from the control device 9 to the camera head 5 individually.

Note that the captured image or the like transmitted from the camera head 5 to the control device 9 via the first transmission cable 6 may be transmitted in an optical signal or in an electrical signal. The similar applies to transmission of the control signal, the synchronization signal, and the clock from the control device 9 to the camera head 5 via the first transmission cable 6.

The display device 7 is implemented by a display using liquid crystal, organic Electro Luminescence (EL), or the like, and displays an image based on a video signal from the control device 9 under the control of the control device 9.

The second transmission cable 8 has one end detachably connected to the display device 7 and the other end detachably connected to the control device 9. The second transmission cable 8 transmits the video signal processed by the control device 9 to the display device 7.

The control device 9 corresponds to the medical image processing device according to the present disclosure. The control device 9 is implemented by a central processing unit (CPU), a Field-Programmable Gate Array (FPGA), or the like, and comprehensively controls operation of the light source device 3, the camera head 5, and the display device 7.

A detailed configuration of the control device 9 will be described in "Configuration of control device" described below.

The third transmission cable 10 has one end detachably connected to the light source device 3 and the other end detachably connected to the control device 9. The third transmission cable 10 transmits the control signal from the control device 9 to the light source device 3.

Figure 2:
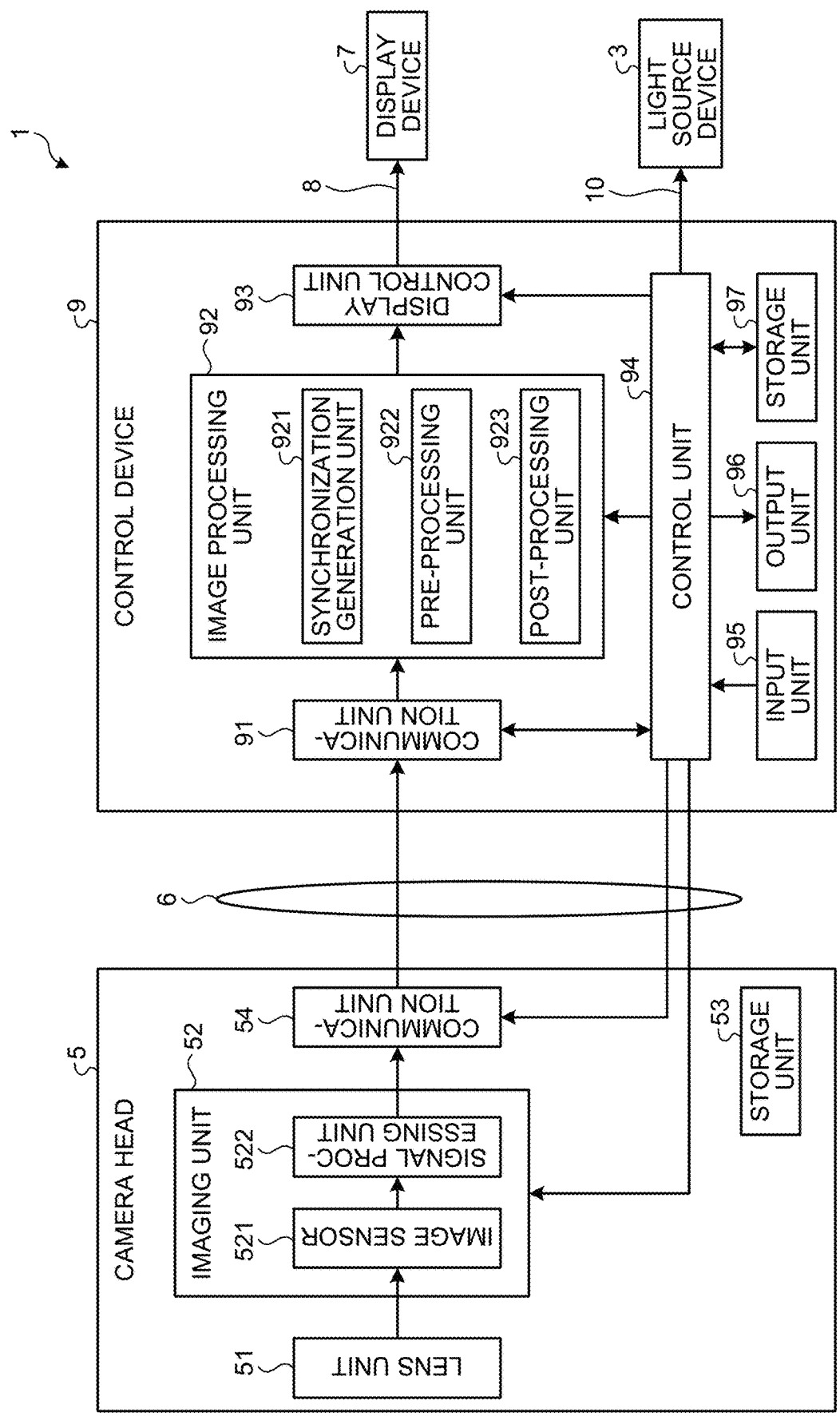
FIG. 2 is a block diagram illustrating a configuration of a camera head and a control device.

Configuration of camera head FIG. 2 is a block diagram illustrating a configuration of the camera head 5 and the control device 9.

Next, a configuration of the camera head 5 will be described with reference to FIG. 2.

As illustrated in FIG. 2, the camera head 5 includes a lens unit 51, an imaging unit 52, a storage unit 53, and a communication unit 54.

The lens unit 51 includes one or more lenses, and forms a subject image condensed by the insertion unit 2 on an imaging surface of the imaging unit 52 (an image sensor 521).

The imaging unit 52 captures the inside of the living body under the control of the control device 9. As illustrated in FIG. 2, the imaging unit 52 includes the image sensor 521 and a signal processing unit 522.

The image sensor 521 is implemented by a Charge Coupled Device (CCD), Complementary Metal Oxide Semiconductor (CMOS) or the like that receives the subject image formed by the lens unit 51 and converts the image into an electrical signal (analog signal).

The signal processing unit 522 performs signal processing on a captured image of an analog signal generated by the image sensor 522 and outputs a captured image of a digital signal.

The storage unit 53 stores a camera head identifier (ID) for uniquely identifying the type of the camera head 5. The camera head ID corresponds to identification information according to the present disclosure.

The communication unit 54 is an interface that communicates with the control device 9 via a first transmission cable 6. The communication unit 54 transmits the captured image (digital signal) output from the imaging unit 52 and the camera head ID stored in the storage unit 53 to the control device 9, and receives a control signal and the like from the control device 9.

Configuration of Control Device

Next, the configuration of the control device 9 will be described with reference to FIG. 2.

As illustrated in FIG. 2, the control device 9 includes a communication unit 91, an image processing unit 92, a display control unit 93, a control unit 94, an input unit 95, an output unit 96, and a storage unit 97.

The communication unit 91 is an interface that communicates with the camera head 5 (communication unit 54) via the first transmission cable 6. Subsequently, the communication unit 91 receives the captured image (digital signal) and the camera head ID output from the communication unit 54, and transmits a control signal and the like from the control unit 94.

Under the control of the control unit 94, the image processing unit 92 executes image processing on the captured image (digital signal) output from the camera head and received by the communication unit 91.

Specific examples of the image processing include optical black subtraction processing, demosaic processing, white balance adjustment processing, noise reduction processing, color correction processing, color enhancement processing, and contour enhancement processing.

As illustrated in FIG. 2, the image processing unit 92 includes a synchronization generation unit 921, a pre-processing unit 922, and a post-processing unit 923.

The synchronization generation unit 921 is a unit that generates a synchronization signal under the control of the control unit 94.

Based on the synchronization signal generated by the synchronization generation unit 921, the pre-processing unit 922 performs some image processing of the image processing except for the noise reduction processing on the captured image (digital signal) received by the communication unit 91.

Based on the synchronization signal generated by the synchronization generation unit 921, the post-processing unit 923 executes image processing such as noise reduction processing, which is not executed by the pre-processing unit 922 among the above-described image processing, on the captured image (digital signal) after the image processing is executed by the pre-processing unit 922.

The function of executing the noise reduction processing in the post-processing unit 923 will be described in "Function of executing noise reduction processing in post-processing unit" described below.

The display control unit 93 generates a display video signal for displaying a captured image after image processing is executed by the image processing unit 92. Subsequently, the display control unit 93 outputs the video signal to the display device 7. With this operation, the captured image is displayed on the display device 7.

The control unit 94 is implemented by executing various programs stored in the storage unit 97 by a controller such as a CPU or a micro processing unit (MPU). The control unit 94 controls the operations of the light source device 3, the camera head 5, and the display device 7 and controls the entire operation of the control device 9. The control unit 94 may be constituted with an integrated circuit such as an application specific integrated circuit (ASIC) or an FPGA, not limited to the CPU or the MPU. The control unit 94 has the function of a processing control unit 941 (refer to FIG. 3) according to the present disclosure. The function will be described in "Execution timing of readout stop processing" described below.

The input unit 95 is constituted with an operation device such as a mouse, a keyboard, and a touch panel, and receives user operations performed by a user such as a doctor. Subsequently, the input unit 95 outputs an operation signal corresponding to the user operation to the control unit 94.

The output unit 96 is constituted with a speaker, a printer, or the like, and outputs various types of information.

The storage unit 97 stores a program executed by the control unit 94, information needed for processing performed by the control unit 94, or the like.

Function of Executing Noise Reduction Processing in Post-Processing Unit

Next, a function of executing the noise reduction processing in the post-processing unit 923 will be described.

Figure 3:
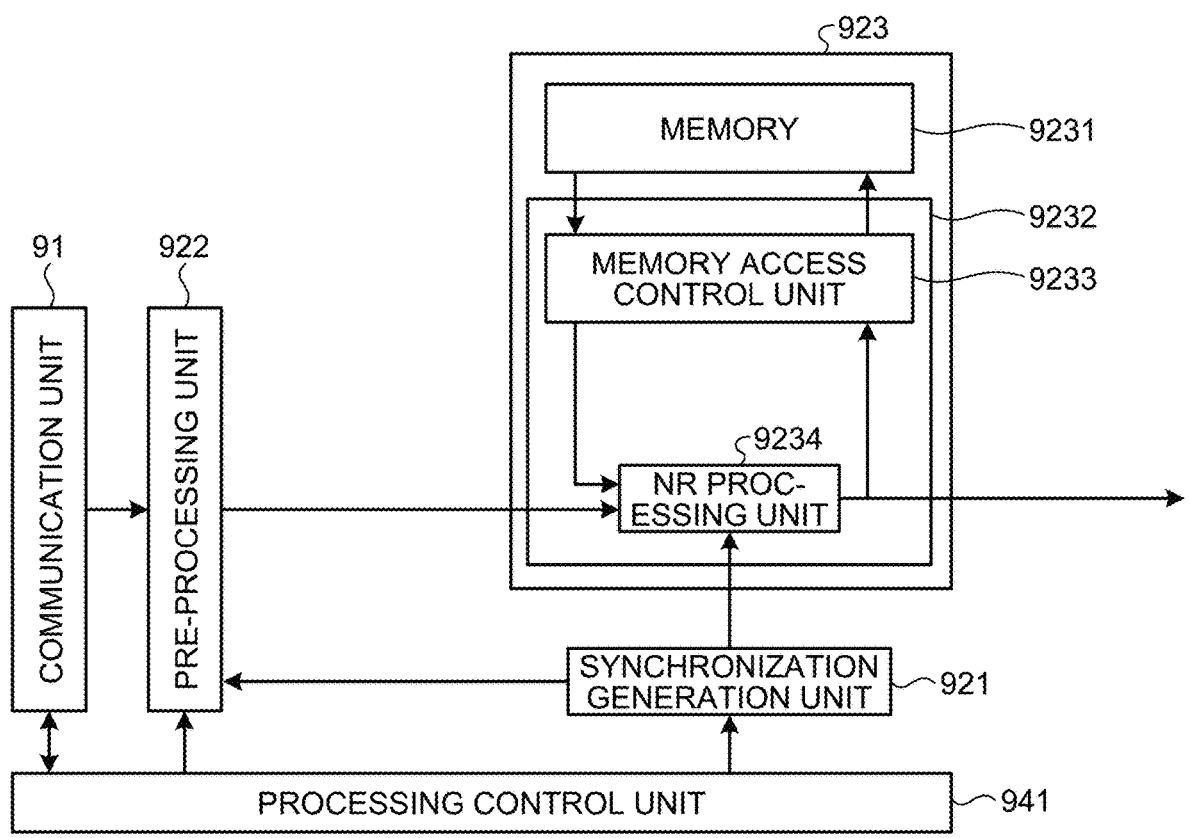
FIG. 3 is a block diagram illustrating a function of executing noise reduction processing performed in a post-processing unit.

FIG. 3 is a block diagram illustrating a function of executing the noise reduction processing in the post-processing unit 923.

As illustrated in FIG. 3, the post-processing unit 923 includes a memory 9231 and a noise processing unit 9232 as functions of executing the noise reduction processing.

The memory 9231 is frame memory that stores a captured image of one frame.

As illustrated in FIG. 3, the noise processing unit 9232 includes a memory access control unit 9233 and a noise reduction processing unit 9234 (hereinafter, referred to as the NR processing unit 9234).

The memory access control unit 9233 executes writing of the captured image to the memory 9231 and reading of the captured image from the memory 9231 individually based on the synchronization signal generated by the synchronization generation unit 921.

The NR processing unit 9234 executes known noise reduction processing of blending a captured image of a current frame input from the pre-processing unit 922 and a captured image of a past frame read out from the memory 9231 at a predetermined blending ratio. For example, the NR processing unit 9234 obtains a correlation between the captured image of the current frame and the captured image of the past frame. When having determined that the correlation is low (for example, in a case where the motion of the subject is large), the NR processing unit 9234 decreases the blending ratio of the captured image of the past frame. In contrast, when having determined that the correlation is high, the NR processing unit 9234 increases the blending ratio of the captured image of the past frame.

Furthermore, the noise processing unit 9232 executes readout stop processing, which is processing of stopping reading the captured image of the past frame from the memory 9231 and writing the captured image of the current frame input from the pre-processing unit 922 to the memory 9231 at a predetermined timing without executing the noise reduction processing described above.

The noise processing unit 9232 described above may be implemented by hardware, software, or a combination of hardware and software.

Execution Timing of Readout Stop Processing

Next, the execution timing of the readout stop processing performed by the noise processing unit 9232 will be described.

Figure 4:
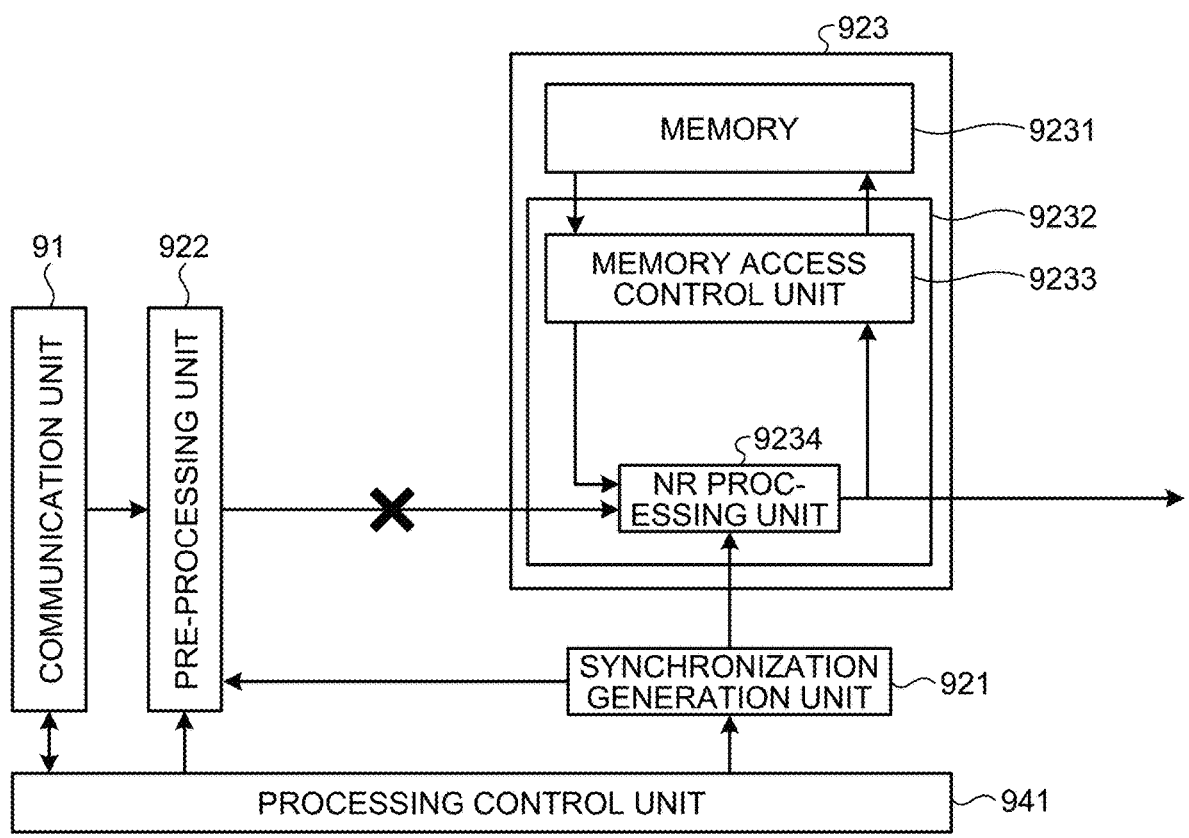
FIG. 4 is a diagram illustrating an execution timing of readout stop processing.
Figure 5:
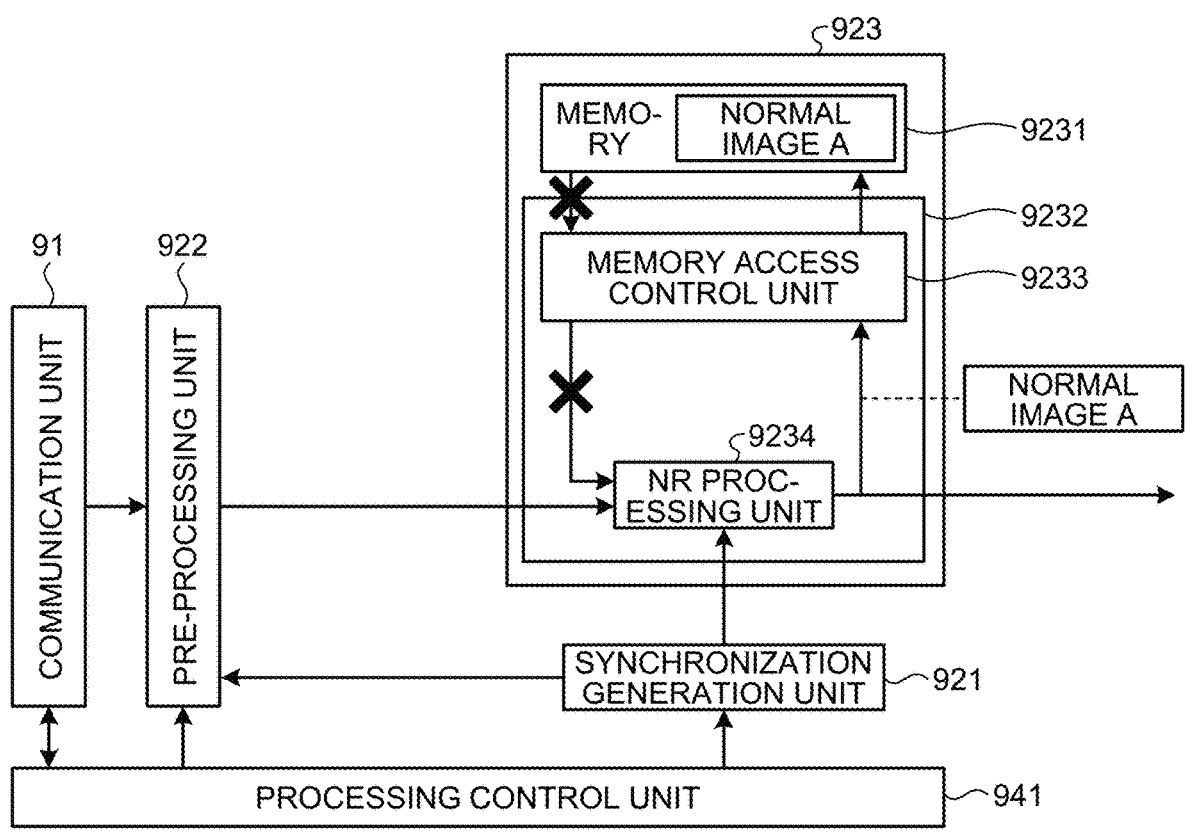
FIG. 5 is a diagram illustrating an execution timing of readout stop processing.
Figure 6:
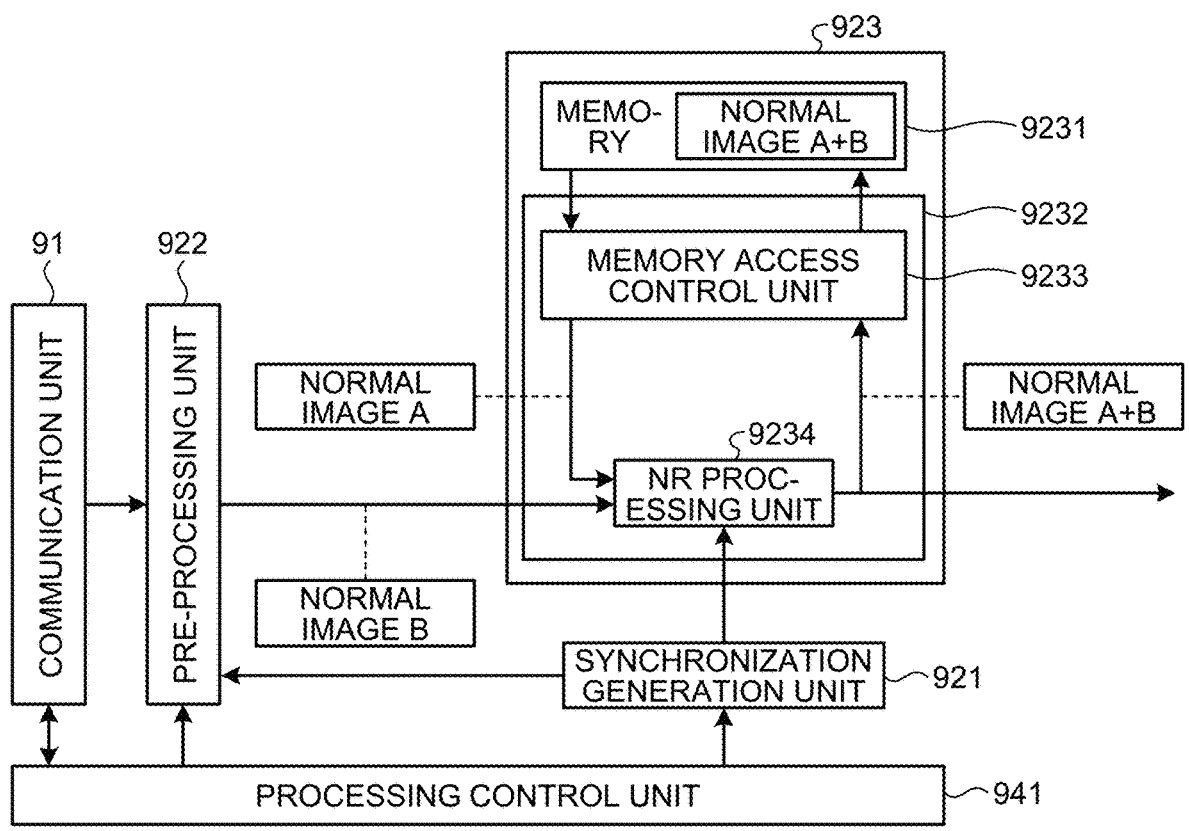
FIG. 6 is a diagram illustrating an execution timing of readout stop processing.

FIGS. 4 to 6 are diagrams illustrating an execution timing of the readout stop processing.

First, the processing control unit 941 determines whether a captured image to be input to the noise processing unit 9232 is to be a stable image.

For example, in a case where a link-up state is established between the camera head 5 (communication unit 54) and the control device 9 (communication unit 91), the processing control unit 941 determines that the captured image input to the noise processing unit 9232 is to be a stable image. In contrast, in a case where a link-up state is not established between the camera head 5 (communication unit 54) and the control device 9 (communication unit 91), the processing control unit 941 determines that the captured image input to the noise processing unit 9232 is not to be a stable image.

Furthermore, for example, in a case where camera head ID is detected via the communication unit 91, the processing control unit 941 determines that the captured image input to the noise processing unit 9232 is to be a stable image. In contrast, in a case where the camera head ID is not detected via the communication unit 91, the processing control unit 941 determines that the captured image input to the noise processing unit 9232 is not to be a stable image.

Subsequently, when having determined that the captured image input to the noise processing unit 9232 is not to be a stable image, as illustrated in FIG. 4, the processing control unit 941 prohibits input of the captured image to the noise processing unit 9232.

Specifically, the processing control unit 941 turns off the function of the pre-processing unit 922. With this operation, the output of the captured image from the pre-processing unit 922 to the noise processing unit 9232 is stopped. FIG. 4 represents a state of stopping the output of the captured image from the pre-processing unit 922 to the noise processing unit 9232 by a "x" mark.

On the other hand, the processing control unit 941 turns on the function of the pre-processing unit 922 at the timing when having determined that the captured image input to the noise processing unit 9232 is to be a stable image. This operation starts output of the captured image from the pre-processing unit 922 to the noise processing unit 9232 as illustrated in FIG. 5. In FIG. 5, a state in which the output of the captured image from the pre-processing unit 922 to the noise processing unit 9232 is started is expressed by deleting the "x" mark illustrated in FIG. 4.

Furthermore, the processing control unit 941 controls the noise processing unit 9232 to execute the readout stop processing at a timing when having determined that the captured image input to the noise processing unit 9232 is to be a stable image.

Specifically, as illustrated in FIG. 5, the noise processing unit 9232 stops readout of the captured image of the past frame from the memory 9231 and writes a normal image A, which is a captured image of the current frame input from the pre-processing unit 922, into the memory 9231 based on the synchronization signal generated by the synchronization generation unit 921 without executing the above-described noise reduction processing. With this operation, even when an indefinite value is stored in the memory 9231, the indefinite value is rewritten by the normal image A. In FIG. 5, a state of stopping the readout of the captured image of the past frame from the memory 9231 is represented by a "x" mark.

Subsequently, under the control of the processing control unit 941, the noise processing unit 9232 executes readout stop processing and thereafter starts execution of noise reduction processing.

Specifically, as illustrated in FIG. 6, the noise processing unit 9232 reads out the normal image A, which is the captured image of the past frame, from the memory 9231 based on the synchronization signal generated by the synchronization generation unit 921, and executes noise reduction processing based on the normal image A and a normal image B, which is a captured image of the current frame input from the pre-processing unit 922. Furthermore, the noise processing unit 9232 reads out the normal image A from the memory 9231 based on the synchronization signal generated by the synchronization generation unit 921, and writes a normal image A+B, which is a captured image that has undergone noise reduction processing.

The present embodiment described above achieves the following effects.

In the control device 9 according to the present embodiment, the noise processing unit 9232 executes the readout stop processing at a predetermined timing.

Therefore, even when an indefinite value is stored in the memory 9231, the indefinite value is rewritten to the captured image, which has been written as the current frame (normal image A illustrated in FIG. 5) into the memory 9231.

By the way, in a case where the noise reduction processing is executed across the input captured image of the current frame and the data of the indefinite value stored in the memory 9231, the following problem might occur.

That is, the noise processing unit 9232 might determine that the correlation between the captured image of the current frame and the data of the indefinite value is high. In this case, the noise processing unit 9232 would increase the blending ratio of the captured image of the past frame by determining the data of the indefinite value as an appropriate captured image of the past frame, leading to a failure in reduction of the noise of the captured image of the current frame, and a failure in obtaining an image suitable for observation.

In view of this, in the present embodiment, the noise processing unit 9232 executes noise reduction processing across the input captured image of the current frame (normal image B illustrated in FIG. 5) and the captured image of the past frame (normal image A illustrated in FIG. 5) which is not the data of the indefinite value stored in the memory 9231.

Accordingly, with the control device 9 of the present embodiment, the noise reduction processing may be executed using the captured image of the appropriate past frame, leading to acquisition of an image suitable for observation.

By the way, when the noise processing unit 9232 executes the readout stop processing in a case where the captured image input to the noise processing unit 9232 is an unstable image, the result on the memory 9231 would be such that indefinite value data is only rewritten into the captured image being an unstable image. That is, in a case where the noise reduction processing is executed across the input captured image of the current frame and the captured image which is the unstable image stored in the memory 9231, there is a possibility of occurrence of a problem similar to the above-described problem occurring when the data of the indefinite value is stored in the memory 9231.

In this regard, the execution timing of the readout stop processing is a timing at which the captured image input to the noise processing unit 9232 is to be a stable image.

Therefore, when the noise processing unit 9232 executes the readout stop processing, data of an indefinite value is rewritten into the captured image being a stable image in the memory 9231. That is, the above-described problem may be effectively solved.

Other Embodiments

While the above is description of the modes for carrying out the present disclosure, the present disclosure should not be limited by only the embodiment described above.

Figure 7:
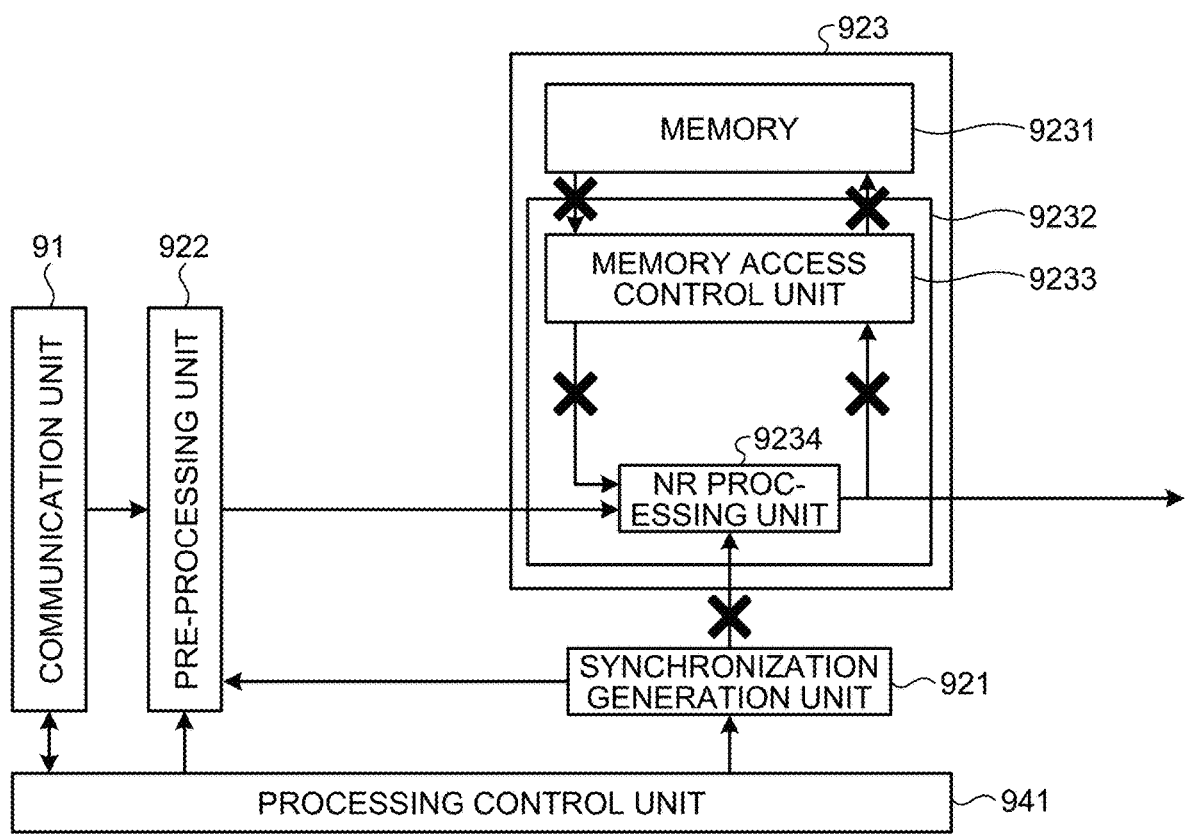
FIG. 7 is a diagram illustrating a modification of the embodiment.

FIG. 7 is a diagram illustrating a modification of the embodiment. Specifically, FIG. 7 is a diagram corresponding to FIG. 4.

In the above embodiment, when having determined that the captured image input to the noise processing unit 9232 is not to be a stable image, as illustrated in FIG. 4, the processing control unit 941 prohibits input of the captured image to the noise processing unit 9232. However, the configuration is not limited to this. For example, when having determined that the captured image input to the noise processing unit 9232 is not to be a stable image, the processing control unit 941 may execute the control according to the present modification illustrated in FIG. 7.

Specifically, when having determined that the captured image input to the noise processing unit 9232 is not to be a stable image, the processing control unit 941 controls the synchronization generation unit 921 to prohibit the synchronization signal from being output from the synchronization generation unit 921 to the noise processing unit 9232. With this configuration, as illustrated in FIG. 7, the noise processing unit 9232 does not execute either writing of the captured image to the memory 9231 or reading of the captured image from the memory 9231. In FIG. 7, a state in which the output of the synchronization signal from the synchronization generation unit 921 to the noise processing unit 9232 is prohibited, and a state in which neither the writing of the captured image to the memory 9231 nor the reading of the captured image from the memory 9231 is to be executed is represented by using "x" marks.

In the above-described embodiment, the function of the processing control unit 941 may be provided in the noise processing unit 9232.

In the above-described embodiment, the noise processing unit 9232 executes processing referred to as temporal noise reduction processing of reducing noise of the captured image of the current frame based on the captured image of the current frame and the captured image of the past frame. However, the configuration is not limited to this. For example, the noise processing unit 9232 may also execute processing referred to as spatial noise reduction processing, being processing of reducing noise of the captured image based on only the captured image of the current frame.

In the above-described embodiments, the medical image processing device according to the present disclosure is mounted on the medical observation system 1 having the insertion unit 2 formed with a rigid endoscope, but the configuration is not limited thereto. For example, the medical image processing device according to the present disclosure may be mounted on a medical observation system having the insertion unit 2 formed with a flexible endoscope. In addition, the medical image processing device according to the present disclosure may be mounted on a medical observation system such as a surgical microscope (refer to JP 2016-42981 A, for example) that enlarges and observes a predetermined field of view inside a living body or on a surface of a living body.

The following configurations also belong to the technical scope of the present disclosure.

(1) A medical image processing device including an image processing unit configured to perform image processing on a captured image obtained by capturing a subject image, the image processing unit including: a memory configured to store the captured image; and a noise processing unit configured to enable execution of writing of the captured image into the memory and readout of the captured image from the memory individually, and execute noise reduction processing of reducing noise of the captured image of the current frame based on the captured image of the current frame that has been input and the captured image of the past frame that has been read out from the memory, the noise processing unit being configured to execute readout stop processing of stopping readout of the past frame from the memory at a predetermined timing and writing the captured image of the current frame into the memory without executing the noise reduction processing.

(2) The medical image processing device according to (1), wherein the predetermined timing is a timing at which the captured image input to the noise processing unit is to be a stable image.

(3) The medical image processing device according to (2), further including a processing control unit configured to determine whether the captured image input to the noise processing unit is to be a stable image, execute the readout stop processing at a timing when it is determined that the captured image is to be a stable image, and start execution of the noise reduction processing after executing the readout stop processing.

(4) The medical image processing device according to (3), wherein in a case where a link-up state is established between a medical observation device that captures a subject image and generates the captured image and the medical image processing device, the processing control unit is configured to determine that the captured image input to the noise processing unit is to be a stable image.

(5) The medical image processing device according to (3), wherein a medical observation device that captures a subject image and generates the captured image is connected to the medical image processing device, and when identification information that is output from the medical observation device and uniquely identifies the medical observation device has been detected, the processing control unit is configured to determine that the captured image input to the noise processing unit is to be a stable image.

(6) The medical image processing device according to (3), wherein when the processing control unit has determined that the captured image input to the noise processing unit is not to be a stable image, the processing control unit is configured to prohibit input of the captured image to the noise processing unit.

(7) The medical image processing device according to (3), wherein, when the processing control unit has determined that the captured image input to the noise processing unit is not to be a stable image, the noise processing unit does not allow the processing control unit to execute writing of the captured image into the memory or readout of the captured image from the memory.

(8) A medical observation system including: a medical observation device configured to capture a subject image to generate a captured image; and a medical image processing device including an image processing unit configured to perform image processing on the captured image, the image processing unit including: a memory configured to store the captured image; and a noise processing unit configured to enable execution of writing of the captured image into the memory and readout of the captured image from the memory individually, and execute noise reduction processing of reducing noise of the captured image of the current frame based on the captured image of the current frame that has been input and the captured image of the past frame that has been read out from the memory, wherein the noise processing unit is configured to execute readout stop processing of stopping readout of the past frame from the memory at a predetermined timing and writing the captured image of the current frame into the memory without executing the noise reduction processing.

According to the medical image processing device and the medical observation system, it is possible to obtain a captured image suitable for observation.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A medical image processing device comprising
an image processing unit configured to perform image processing on a captured image obtained by capturing a subject image, the image processing unit including:
a memory configured to store the captured image; and
a noise processing unit configured to
enable execution of writing of the captured image into the memory and readout of the captured image from the memory individually, and
execute noise reduction processing of reducing noise of the captured image of the current frame based on the captured image of the current frame that has been input and the captured image of the past frame that has been read out from the memory, the noise processing unit being configured to execute readout stop processing of stopping readout of the past frame from the memory at a predetermined timing and writing the captured image of the current frame into the memory without executing the noise reduction processing.

2. The medical image processing device according to claim 1, wherein the predetermined timing is a timing at which the captured image input to the noise processing unit is to be a stable image.

3. The medical image processing device according to claim 2, further comprising a processing control unit configured to
determine whether the captured image input to the noise processing unit is to be a stable image,
execute the readout stop processing at a timing when it is determined that the captured image is to be a stable image, and
start execution of the noise reduction processing after executing the readout stop processing.

4. The medical image processing device according to claim 3, wherein in a case where a link-up state is established between a medical observation device that captures a subject image and generates the captured image and the medical image processing device, the processing control unit is configured to determine that the captured image input to the noise processing unit is to be a stable image.

5. The medical image processing device according to claim 3, wherein a medical observation device that captures a subject image and generates the captured image is connected to the medical image processing device, and when identification information that is output from the medical observation device and uniquely identifies the medical observation device has been detected, the processing control unit is configured to determine that the captured image input to the noise processing unit is to be a stable image.

6. The medical image processing device according to claim 3, wherein when the processing control unit has determined that the captured image input to the noise processing unit is not to be a stable image, the processing control unit is configured to prohibit input of the captured image to the noise processing unit.

7. The medical image processing device according to claim 3, wherein, when the processing control unit has determined that the captured image input to the noise processing unit is not to be a stable image, the noise processing unit does not allow the processing control unit to execute writing of the captured image into the memory or readout of the captured image from the memory.

8. A medical observation system comprising:
- a medical observation device configured to capture a subject image to generate a captured image; and
- a medical image processing device including an image processing unit configured to perform image processing on the captured image, the image processing unit including:
  - a memory configured to store the captured image; and
  - a noise processing unit configured to
    - enable execution of writing of the captured image into the memory and readout of the captured image from the memory individually, and
    - execute noise reduction processing of reducing noise of the captured image of the current frame based on the captured image of the current frame that has been input and the captured image of the past frame that has been read out from the memory, wherein the noise processing unit is configured to execute readout stop processing of stopping readout of the past frame from the memory at a predetermined timing and writing the captured image of the current frame into the memory without executing the noise reduction processing.

* * * * *